United States Patent
Bunel et al.

(10) Patent No.: US 6,365,770 B1
(45) Date of Patent: Apr. 2, 2002

(54) PRODUCTION OF ALKYL 6-AMINOCAPROATE

(75) Inventors: Emilio E. Bunel; Theodore A. Koch, both of Wilmington; Ronnie Ozer, Arden; Sourav K. Sengupta, Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/713,153

(22) Filed: Nov. 16, 2000

(51) Int. Cl.[7] .............................................. C07C 229/00
(52) U.S. Cl. ....................................... 560/155; 560/208
(58) Field of Search .......................................... 560/155

(56) References Cited

U.S. PATENT DOCUMENTS

| | | | |
|---|---|---|---|
| 3,496,215 A | | 2/1970 | Drinkard et al. |
| 4,470,928 A | * | 9/1984 | Kimura et al. ............ 260/239.3 |
| 4,518,796 A | * | 5/1985 | Aoshima et al. ............ 560/208 |
| 5,618,983 A | * | 4/1997 | Burke ........................ 568/454 |
| 5,821,378 A | | 10/1998 | Foo et al. |
| 5,986,126 A | | 11/1999 | Bunel et al. |
| 6,048,997 A | | 4/2000 | Fischer et al. |
| 6,069,246 A | | 5/2000 | Chiarelli et al. |

OTHER PUBLICATIONS

Oxidations in Organic Chemistry, Hudlicky (1990) p. 174.*
March, Jerry, Advanced Organic Chemistry, Reactions, Mechanisms, and Structure, 1992, pp. 887–888, John Wiley & Sons, NY, USA.

* cited by examiner

*Primary Examiner*—Gary Geist
*Assistant Examiner*—Zachary Tucker

(57) ABSTRACT

A process for making alkyl 6-aminocaproate by hydroformylating 3-pentenenitrile to produce 3-, 4-, and 5-formylvaleronitrile (FVN mixture), converting the FVN mixture to alkyl 3-, 4-, and 5-cyanovalerate by either oxidative esterification of the FVN mixture or oxidation of the FVN mixture followed by esterification; isolating alkyl 5-cyanovalerate; and hydrogenating the alkyl 5-cyanovalerate to produce alkyl 6-aminocaproate. The resulting alkyl 6-aminocaproate can be cyclized to produce caprolactam.

20 Claims, No Drawings

PRODUCTION OF ALKYL 6-AMINOCAPROATE

FIELD OF THE INVENTION

The present invention concerns a process to produce alkyl 6-aminocaproate and/or caprolactam.

BACKGROUND OF THE INVENTION

Commercially, caprolactam is made by a process using cyclohexane as the starting material. Caprolactam is then polymerized to produce nylon-6. For cost reasons, it would be desirable to produce caprolactam with butadiene, a four carbon starting material, rather than the six carbon cyclohexane starting material currently used in commercial processes.

It is known that butadiene can be reacted with HCN to produce 3-pentenenitrile (3PN). One process for converting 3PN to caprolactam involves converting 3PN to adiponitrile (ADN). ADN is then partially hydrogenated to 6-aminocapronitrile, which is then converted to caprolactam by hydrolysis followed by cyclization. See for example, U.S. Pat. No. 6,069,246. The partial hydrogenation reaction produces a significant amount of hexamethylenediamine (HMD).

A second process for converting 3PN to caprolactam involves reductive amination of 5-formylvaleronitrile that is derived by hydroformylation of 3-pentenenitrile. The reductively aminated product is then subjected to hydrolysis and cyclized. U.S. Pat. No. 6,048,997 discloses a process in which a mixture containing 2-, 3-, and 4-pentenenitrile is reacted with carbon monoxide and hydrogen in the presence of a catalyst containing at least one Group VIII metal to produce a mixture comprising 3-, 4-, and 5-formylvaleronitrile. U.S. Pat. No. 5,986,126 teaches that 5-formylvaleronitrile is unstable and that the separation of 5-formylvaleronitrile from the branched 3- and 4-formylvaleronitriles is impractical because of yield losses that are suffered in distillation. To avoid this problem, U.S. Pat. No. 5,986,126 teaches that the separation of the linear product from the branched isomers is possible downstream after reductive amination of the formylvaleronitriles to produce aminonitriles (such as 6-aminocapronitrile) and diamines. In this second process, a significant amount of HMD is produced.

Both of the two 3PN-based processes described above produce significant amounts of HMD. It is not always desired to have HMD as a co-product in a commercial caprolactam operation. Thus, there is a need for a process that converts butadiene to caprolactam without the production of significant amounts of HMD. The present invention provides such a process.

BRIEF SUMMARY OF THE INVENTION

The present invention is a 3PN-based process for making alkyl 6-aminocaproate that does not produce significant amounts of HMD. The present invention accomplishes this by a process comprising:

(a) reacting 3-pentenenitrile with carbon monoxide and hydrogen in the presence of a hydroformylation catalyst comprising a Group VIII metal to produce a first reaction product which comprises 3-, 4-, and 5-formylvaleronitrile (FVN);

(b) isolating from the first reaction product a FVN mixture consists essentially of 3-, 4-, and 5-formylvaleronitrile;

(c) reacting the FVN mixture to produce a second reaction product which comprises alkyl 3-, 4-, and 5-cyanovalerate by either:

(i) contacting the FVN mixture with an alcohol, a molecular oxygen-containing gas, and a palladium-containing catalyst for a time sufficient to oxidize the FVN mixture to produce the second reaction product, or (ii) oxidizing the FVN mixture in the presence of a molecular oxygen-containing gas for a time sufficient to oxidize the FVN mixture to produce an oxidation product comprising 3-, 4-, and 5-cyanovaleric acid, and reacting the oxidation product with an alcohol to produce the second reaction product;

(d) isolating the alkyl 5-cyanovalerate by distillation, and (e) reacting alkyl 5-cyanovalerate with hydrogen in the presence of a hydrogenation catalyst to produce a third reaction product which comprises alkyl 6-aminocaproate, the alkyl group of which contains the same number of carbon atoms as the alcohol.

DETAILED DESCRIPTION OF THE INVENTION

The present invention concerns a process for the production of alkyl 6-aminocaproate. Suitable alkyl groups are $C_1$ to $C_{12}$ linear or branched alkyl groups. Preferably the alkyl group is methyl or ethyl. More preferably, the alkyl group is methyl.

Production of 3-Pentenenitrile

3-Pentenenitrile (3PN) is produced commercially as an intermediate in the production of adiponitrile. The synthesis of 3PN is well known in the art. See for example, U.S. Pat. Nos. 3,496,215 and 5,821,378, the disclosures of which are incorporated herein by reference.

Hydroformylation of 3-Pentenenitrile

The hydroformylation of 3-pentenenitrile (i.e., the reaction of 3-pentenenitrile with carbon monoxide and hydrogen) to produce a reaction product which comprises 3-, 4-, and 5-formylvaleronitrile (FVN) is carried out in the presence of a catalyst comprising a Group VIII element. The hydroformylation reaction temperature can vary from room temperature to about 200° C., preferably between 50 and 150° C. The pressure is preferably between 0.15 and 10 MPa and more preferably 0.2 to 5 MPa.

Preferred catalysts are rhodium compounds. Examples of suitable compounds include Rh(CO) 2 (DPM), [DPM=t—$C_4H_9$—COCHCO—t—$C_4H_9$]; $Rh(CO)_2(acac)$, [acac= acetylacetonate]; $Rh_2O_3$; $Rh_4(CO)_{12}$; $Rh_6(CO)_{16}$; $[Rh(OAc)_2]_2$, [OAc=acetate]; and $Rh(ethylhexanoate)_2$. Preferably, the catalyst is $Rh(CO)_2(acac)$, $Rh(CO)_2(DPM)$, or $[Rh(OAc)_2]_2$.

These catalysts can be used in combination with phosphorous-containing ligands such as monodentate or bidentate phosphine, phosphonites, phosphinites, or phosphite compounds. Examples of such ligands include triarylphosphites, such as triphenylphosphite; triarylphosphines, such as triphenylphosphine; and bis (diarylphosphino)alkanes, such as diphenylphosphinoethane. In addition, polydentate phosphite compounds may be used as ligands. An example of these includes compounds having a structural formula as follows:

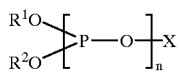

where $R^1$ and $R^2$ are the same or different mono-valent aryl groups, X is an n-valent organic bridging group, and n is an integer between 2 and 6. $R^1$ and $R^2$ may be substituted. Such ligands are described, for example, in U.S. Pat. No. 5,710,344, the disclosure of which is incorporated herein by reference.

The mole ratio of 3-pentenenitrile to catalyst is generally 100:1 to 100,000:1, preferably 500:1 to 10,000:1. The mole ratio of ligand to rhodium is typically between 0.5:1 and 10:1.

The mole ratio of hydrogen to carbon monoxide for hydroformylation reactions is typically in the range of 100:1 to 1:10, preferably in the range of 4.0:1 to 0.5:1. Inert gases may also be present in the hydrogen and carbon monoxide feed stocks.

The hydroformylation reaction may be performed in the presence of a solvent. Suitable solvents include inert solvents or a solvent consisting of the hydroformylation products themselves. Suitable inert solvents include aromatic hydrocarbons, aliphatic hydrocarbons, nitriles, ethers, amides and urea derivatives, saturated hydrocarbons, and ketones. Some examples of suitable solvents include toluene, cyclohexane, benzene, xylene, Texanol® (2,2,4-trimethyl-1,3-pentanediol monoisobutyrate), diphenylether, tetrahydrofuran, cyclohexanone, benzonitrile, N-methylpyrrolidinone, and N,N-dimethylethylurea.

The hydroformylation reaction can be performed in a continuous or batch mode. The reaction can be performed in a variety of reactors, such as bubble column reactors, continuously stirred tank reactors, trickle bed reactors, and liquid-overflow reactors. Unreacted hydrogen, carbon monoxide, 3-pentenenitrile, and any solvent may be recovered and recycled to the hydroformylation reactor.

The hydroformylation reaction product comprises 3-, 4-, and 5-formylvaleronitriles, as well as unconverted 2-, 3-, and 4-pentenenitrile, catalyst, and high boilers. The separation of the FVN mixture from the catalyst and high boilers can be effected by utilizing thermally gentle evaporation techniques, known to those skilled in the art. Such techniques include the use of single stage flash evaporators, such as rolling-film evaporators, falling-film evaporators, or wiped-film evaporators. High boilers and catalyst separated from the FVN mixture can be recycled back to the hydroformylation reactor.

To avoid the decomposition of the catalyst and FVN mixture, a short contact time during flash evaporation is generally preferred. The contact time can vary between 1 second and 1 hour and preferably is between 1 and 5 minutes. The flash evaporation is carried out under commercially viable operating conditions. The temperature should be in the range of 75 to 200° C. The preferred range is 100 to 130° C. The pressure can vary from 13.3 to 1333 Pa, preferably 66.6 to 666.5 Pa.

Oxidative Esterification of 5-Formylvaleronitrile

Alkyl 5-cyanovalerate can be made by oxidative esterification of 5-formylvaleronitrile (5-FVN or 5FVN). In this process, 5-FVN is exposed to an alcohol and an oxygen containing gas in the presence of a palladium-containing catalyst.

The FVN mixture is contacted with a molecular oxygen-containing gas for a time sufficient to oxidize the FVN mixture to produce a reaction product containing alkyl 3-, 4-, and 5-cyanovalerate (mixed ACV). Preferably, the oxidation is performed at a pressure of 100 to 5000 psig (0.7 to 34.5 MPa) in the presence of air. More preferably, the pressure is 500 to 2000 psig (3.4 to 13.8 MPa). Such reaction conditions give a high conversion rate. The reaction may be run as a continuous process.

The oxidative esterification step of the present invention can be performed at a temperature of from about 20° C. to about 120° C. Preferably, the temperature is in the range of about 40° C. to about 80° C. Since the oxidative esterification is exothermic, operating a commercial reactor at about 50° C., and above, is preferred as heat removal and associated cost become economic considerations. It is preferable to choose a temperature that allows the use of normal, low-cost cooling water.

The alcohol used in the oxidative esterification may be any alcohol that does not interfere with subsequent reaction steps. Preferably, the alcohol is a linear or branched $C_1$ to $C_{12}$ alcohol. More preferably, the alcohol is methanol or ethanol. The reaction can advantageously be run in the presence of a stochiometric excess of alcohol.

Suitable solvents for the oxidative esterification can be selected from the group consisting of aliphatic hydrocarbons, aromatic hydrocarbons, alcohols and esters. Of particular importance are alcohols that can also function as the solvent for the oxidative esterification. The alcohol to aldehyde ratio ranges from 1:1 to 50:1.

The palladium-containing catalyst may be any palladium catalyst capable of catalyzing oxidative esterification of 5-formylvaleronitrile. Preferably, the catalyst is a heterogeneous palladium-based catalyst as described in European Patent Application 199530. Examples of suitable catalysts include $Pd_4TeZnPb$, $Pd_4TeZnPbBi$, and $Pd_4TeZn$.

The actual method of commercially implementing the oxidative esterification process according to the present invention can be by any air oxidation method, as generally known in the art, including, by way of example, but not by limitation, batch reactor with or without stirring, continuous reactor with plug flow or back-mixing, counter current reactor and the like.

Alkyl 5-cyanovalerate can be separated from the reaction mixture by fractional distillation. A stage of evaporation would be used to separate the much lower boiling alcohol (methanol is preferred) from the bulk of the product from oxidative esterification. This separation would be accomplished at a pressure of $1.3 \times 10^{-3}$ MPa to $6.5 \times 10^{-2}$ MPa preferably, $6.5 \times 10^{-3}$ MPa to $3.5 \times 10^{-2}$ MPa. Evaporator temperature would be set to permit near complete removal of methanol, 80 to 200° C., more preferably 100 to 150° C. The methanol rich distillate stream would be recycled to the oxidative esterification. The mixed ACV product, thermally stable compounds now free of methanol, would then be refined in a traditional staged distillation column.

The mixed ACV product is a mixture comprising alkyl-5-cyanovalerate and its branched isomers, alkyl-4-cyanovalerate, and alkyl-3-cyanovalerate. The mixture may be distilled at a pressure of $1.3 \times 10^{-3}$ MPa to $6.5 \times 10^{-2}$ MPa preferably, $6.5 \times 10^{-3}$ MPa to $3.5 \times 10^{-2}$ MPa. In one possible configuration of the process, the mixed ACV stream is fed to the middle section of a distillation column. The branched materials are taken overhead and can be burned or converted to specialty chemicals. The refined linear material exits the column reboiler and can be fed directly to hydrogenation. Typically, the column temperatures are between 100 and 250° C., preferably 140 to 200° C.

Oxidation of FVN Followed by Esterification

As an alternative to oxidative esterification, the FVN mixture can be oxidized in the absence of an alcohol and then esterified. 5-Cyanovaleric acid can be made by oxidation of 5-formylvaleronitrile by a process similar to that taught in U.S. Pat. No. 5,840,959, where methyl-5-formylvalerate is oxidized to produce monomethyladipate.

The FVN mixture is contacted with a molecular oxygen-containing gas for a time sufficient to oxidize the FVN mixture to produce a reaction product containing 3-, 4-, and 5-cyanovaleric acid. FVN can be oxidized with or without a catalyst and at atmospheric or elevated pressure. U.S. Pat. Nos. 4,537,987 and 4,931,590 teach that alkali metal oxides (such as potassium hydroxide or sodium hydroxide in amounts of 0.001 to 0.5% by weight) and metal salts of cobalt or manganese (such as cobalt acetate or manganese acetate in amounts of 0.0001 to 0.1% by weight) can be used to accelerate the oxidation reaction. While these catalysts can be used with the present invention, it is preferred to run the oxidation reaction in the absence of such catalysts.

Preferably, the oxidation is performed at elevated pressure in the presence of air. Such reaction conditions give a high conversion rate. The reaction may be run as a continuous process.

To obtain high conversion and selectivity, a pressure above atmospheric pressure (about 1 MPa) and preferably above 10 bars (1 MPa) of air is required. More preferably, the total pressure when using air should be about 20 bars (2 MPa) or higher. While higher pressures, e.g., 40 to 65 bars (4 to 6.5 MPa), may improve reactivity, they can necessitate higher equipment cost. Pressures of from about 20 to 40 bars (2 to 4 MPa) air represent a realistic and commercially acceptable range.

The oxidation step of the present invention can be performed at a temperature of from about 20° C. to as high as about 120° C. Preferably, the temperature is in the range of about 40° C. to about 80° C. Since the oxidation is exothermic, operating a commercial reactor at about 50° C., and above, is preferred as heat removal and associated cost become economic considerations. It is preferable to choose a temperature that allows the use of normal, low-cost cooling water.

The actual method of commercially implementing the oxidation process according to the present invention can be by any non-catalytic, heterophase, air oxidation method, as generally known in the art, including, by way of example, but not by limitation, batch reactor with or without stirring, continuous reactor with plug flow or back-mixing, counter current reactor and the like. U.S. Pat. No. 5,840,959 teaches that for oxidation of alkyl 5-formylvalerate, realistic heat removal considerations cause the preferred method of reactor operation to be at less than optimum conversion. However, due to the high boiling point of the 3-, 4-, and 5-cyanovaleric acids in the present invention, it is preferred to run the oxidation reaction at the highest possible conversion and selectivity. Such an operation avoids the need to run a recycle loop with its associated distillation requirements.

Following the oxidation, the product can be esterified. Organic esters can be made by reaction of the appropriate carboxylic acid and alcohol in the presence of a homogeneous or heterogeneous catalyst. One of the most common homogeneous catalysts is sulfuric acid, and the most common heterogeneous catalysts are ion-exchange resins. Heterogeneous acidic catalysts have proved to be useful in many applications because of their activity, selectivity, reusability, non-corrosivity and virtual absence of effluent treatment which is associated with the homogeneous catalysts. In the present invention the esterification process is conducted in the presence of primary alcohols having from 1 to 4 carbon atoms. The temperature required for operation ranges from 25 to 150° C. with the preferred range being 70 to 120° C. In order to achieve high yields of esters the reaction between the acid and the ester is conducted in the presence of excess alcohol. The preferred catalysts used are the sulfonic type cation exchange resins, having a macroreticular structure. As the name implies, these are used in their acid form. These catalysts, their properties and method of preparation are taught in U.S. Pat. No. 3,037,052. The catalysts are available commercially and are sold under the trademark Amberlyst-15 (Rohm & Haas Company). The reaction is carried out in a non-aqueous system, the reactants and catalyst being substantially anhydrous. The reaction can be carried out either in batch or continuous manner.

In the present invention, the mixture of 3-, 4-, and 5-cyanovaleric acids is reacted with a linear or branched $C_1$ to $C_{12}$ alcohol to produce a mixture of alkyl 3-, 4-, and 5-cyanovalerate. More preferably, the alcohol is methanol or ethanol. Alkyl 5-cyanovalerate is isolated from the reaction mixture by fractional distillation as described in the preceding discussion of oxidative esterification.

Hydrogenation of Methyl 5-Cyanovalerate

Hydrogenation of the nitrile group to produce alkyl 6-aminocaproate from alkyl 5-cyanovalerate, can be accomplished in the presence of a metal catalyst, and optionally in a liquid solvent. Suitable metal catalysts can be of many types. The catalyst is used in an amount effective to catalyze the reaction. For example, sponge metal catalysts, homogeneous catalysts, and reduced metal oxide and mixed metal oxide catalysts may be used. Supported metal catalysts may be also used. Suitable active metals include iron, ruthenium, rhodium, iridium, palladium, cobalt, nickel, chromium, osmium, and platinum.

Sponge metals are one class of catalysts useful for the present invention. A sponge metal has an extended "skeleton" or "sponge-like" structure of metal, with dissolved aluminum, and optionally contains promoters. The sponge metals may also contain surface hydrous oxides, absorbed hydrous radicals, and hydrogen bubbles in pores. Sponge metal catalysts can be made by the process described in U.S. Pat. No. 1,628,190, the disclosure of which is incorporated herein by reference.

Preferred sponge metals include nickel, cobalt, iron, ruthenium, rhodium, iridium, palladium, and platinum. Sponge nickel or sponge cobalt are particularly suitable as catalysts. The sponge metal may be promoted by one or more promoters selected from the group consisting of Group IA (lithium, sodium, and potassium), IB (copper, silver, and gold), IVB (titanium and zirconium), VB (vanadium), VIB (chromium, molybdenum, and tungsten), VIIB (manganese, rhenium), and VIII (iron, cobalt, nickel, ruthenium, rhodium, palladium, osmium, iridium, and platinum) metals. The promoter can be used in an amount useful to give desired results. For example, the amount of promoter may be any amount less than 50% by weight of the sponge metal, preferably 0 to 10% by weight, more preferably 1 to 5% by weight.

Sponge nickel catalysts contain mainly nickel and aluminum. The aluminum is typically in the form of metallic aluminum, aluminum oxides, and/or aluminum hydroxides. Small amounts of other metals may also be present either in their elemental or chemically bonded form, such as iron and/or chromium, and may be added to the sponge nickel to increase activity and selectivity for the hydrogenation of certain groups of compounds. It is particularly preferred to use chromium and/or iron promoted sponge nickel as a catalyst.

Sponge cobalt catalysts also contain aluminum and may contain promoters. Preferred promoters are nickel and chromium, for example in amounts of about 2% by weight based on the weight of the catalyst.

Examples of suitable sponge metal catalysts include Degussa BLM 112W, W. R. Grace Raney® 2400, Activated Metals A-4000™, and W. R. Grace Raney® 2724.

Supported metal hydrogenation catalysts are another kind of useful catalysts for the present invention. Such catalysts consist of a metal catalyst on a solid support. Any such catalyst may be used in catalytically effective amounts. Preferred metals in the supported metal catalyst include ruthenium, nickel, cobalt, iron, rhodium, iridium, palladium, and platinum. Ruthenium is especially preferred. More than one metal may be used. Any solid support that does not interfere with the reaction can be used. Preferred solid supports include titanium dioxide, porous aluminum oxide, silicon dioxide, aluminum silicate, lanthanum oxide, zirconium dioxide, activated charcoal, aluminum silicate, silicon dioxide, lanthanum oxide, magnesium oxide, zinc oxide, and zeolites.

Particularly preferred solid supports are titanium dioxide, porous aluminum oxide, silicon dioxide, zirconium dioxide, and activated charcoal. Especially useful supported metal catalysts are supported ruthenium catalysts, for example, ruthenium on titanium dioxide. Also, it is acceptable to use a mixture of more than one support and/or more than one catalyst element.

Any method of placing the metal on the support may be used. Several methods are known in the art. One method uses vapor deposition of the metal onto the support. Another method uses a flame spray technique to apply the metal to the support. Another method applies a solution of the metal salt or metal oxide to the support. This step is followed by drying of the support and then reducing the salt or oxide. Another method applies a metal salt that can easily be thermally decomposed to the support. Suitable metal salts include carbonyl or hydride complexes of one or more of iron, nickel, cobalt, ruthenium, rhodium, palladium, osmium, iridium, platinum, chromium, molybdenum, tungsten, manganese, rhenium, copper, silver, and gold.

The metal is typically applied to the solid support at 0.1 to 90 percent by weight relative to the total weight of the supported catalyst. Preferably, the metal is at 0.5 to 50% by weight, more preferably 2 to 25% by weight.

Homogeneous catalysts are another useful type of metal catalyst for the present invention. Homogeneous catalysts are soluble metal compounds incorporating one or a combination of metals such as rhodium, ruthenium, cobalt, nickel, iron, palladium, or platinum, and a hydrocarbon containing ligand which may also contain an atom bonded to the metal atom such as phosphorus, nitrogen, oxygen, carbon, and sulfur.

Another type of useful hydrogenation catalyst is derived from the reduction of at least one metal oxide, a mixture of metal oxides, or a mixture of metal oxide, hydroxide and/or carbonate. Such catalysts have similar structures to sponge metal catalysts in their extended "skeleton" metallic structure. However, they typically would not contain dissolved aluminum or silicon. Such catalysts can be prepared by the reduction of bulk metal oxides such as iron oxide or cobalt oxide. Alternately, the bulk metal oxide precursor may be prepared as a mixture of metal oxides including one or more of the oxides of iron, cobalt, nickel, ruthenium, rhodium, palladium, osmium, iridium, platinum, chromium, molybdenum, tungsten, and manganese. In addition, metal hydroxides or metal carbonates may be included in the metal oxide mixture. See International Patent Application WO 98/04515 and U.S. Pat. No. 6,005,145, the latter being incorporated herein by reference.

The hydrogenation reaction is normally performed at a pressure of 100 to 5000 psi (0.69 to 34.5 MPa), preferably 300 to 1500 psi (2.1 to 10.3 MPa), and more preferably 500 to 1000 psi (3.4 to 6.9 MPa). The hydrogen partial pressure is typically 50 to 4000 psi (0.34 to 27.6 MPa), preferably 100 to 1000 psi (0.69 to 6.9 MPa), and more preferably 250 to 750 psi (1.7 to 5.2 MPa). The molar ratio of hydrogen to alkyl 5-cyanovalerate is typically 2:1 to 200:1, more preferably, 2:1 to 100:1.

The hydrogenation reaction temperature is 40 to 220° C., preferably 70 to 150° C., more preferably 80 to 120° C.

The reaction is preferably carried out in the absence of air.

The hydrogenation reaction may optionally be performed in the presence of a solvent. Any solvent that does not interfere with the reaction may be used and can be used in an amount to increase the yield of the reaction and/or to remove heat from the reaction. Suitable solvents include water, alcohols, esters, hydrocarbons, tetrahydrofuran (THF), dioxane, ammonia, and ammonium hydroxide. Preferred solvents are ammonia, methanol, water, and mixtures of these solvents. Typically when a solvent is used, the mole ratio of solvent to alkyl 5-cyanovalerate is 1:1 to 100:1, preferably 5:1 to 40:1, more preferably 10:1 to 20:1.

Hydrogenation reactions may be performed in any suitable type of reactor. Suitable reactors include a fixed bed reactor and slurry reactor. A fixed bed reactor has an advantage of easy separation of the reactants and products from the catalyst. Slurry reactors include batch, a continuously stirred tank reactor, and a bubble column reactor. In slurry reactors, the catalyst may be removed from the reaction mixture by filtration or centrifugal action.

The amount of hydrogenation catalyst used will depend on the type of reactor used. For slurry reactors, the catalyst will make up 0.1 to about 30% by weight of the reactor contents. Preferably, the amount of catalyst will be 1 to 15% by weight, more preferably 5 to 10% by weight.

For a fixed bed reactor, the weight hourly space velocity will typically fall in the range of 0.05 to 100 $hr^{-1}$, preferably 0.1 to 10 $hr^{-1}$, more preferably 1.0 to 5.0 $hr^{-1}$.

Cyclization of Alkyl 6-Aminocaproate to Produce ε-Caprolactam

U.S. Pat. No. 4,730,040, incorporate herein by reference, describes a process where alkyl 6-aminocaproate can be hydrolyzed to 6-aminocaproic acid which can be cyclized to ε-caprolactam at elevated temperatures (specifically 150 to 370° C.). U.S. Pat. No. 5,877,314, incorporated herein by reference, discloses a process where an alkyl 6-aminocaproate is converted to caprolactam and caprolactam precursors by reaction of alkyl 6-aminocaproate with hydrogen and excess ammonia in the presence of a ruthenium catalyst. The alcohol, typically methanol, is removed from the reaction mixture prior to cyclization.

EXAMPLES

The present invention is exemplified by the following non-limiting examples.

Example 1

Oxidative Esterification of Formylvaleronitriles to Methyl Cyanovalerates

This example shows that formylvaleronitriles can be converted in one step to methyl cyanovalerates (MCV) while the selectivity towards linear isomers increases.

A sample of a solution containing 2.3 g of formylvaleronitriles (84.4% 5FVN, 3.7% 4FVN and 11.8% of 3FVN), 10 g of methanol and 0.5 g of orthodichlorobenzene (GC internal standard) was heated at 50° C. under 500 psig of air for 1 hour in the presence of 10% by weight of a solid catalyst (shown in Table 1). The products were analyzed by Gas Chromatography with a Restex®-5 Amine column (15 m×0.25 mm). The conversions are shown in Table 1. In this table FVN linearity=100*5FVN/(3FVN+4FVN+5FVN). MCV linearity=100*M5CV/(M3CV+M4CV+M5CV).

TABLE 1

|  | $Pd_4TeZnPb$ | $Pd_4TeZnPbBi$ | $Pd_4TeZn$ |
|---|---|---|---|
| 3FVN (mole %) | 5.7 | 7.8 | 5.8 |
| 4FVN (mole %) | 1.7 | 2.1 | 1.8 |
| 5FVN (mole %) | 34.7 | 52.2 | 40.8 |
| M3CV (mole %) | 0.3 | 0.2 | 0.3 |
| M4CV (mole %) | 1.0 | 0.7 | 0.9 |
| M5CV (mole %) | 56.6 | 37.0 | 10.4 |
| Conversion (%) | 53.6 | 35.1 | 49.5 |
| FVN linearity | 82.5 | 84.0 | 84.2 |
| MCV linearity | 97.8 | 97.7 | 97.7 |

Example 2

Separation of Linear and Branched Methyl Cyanovalerates

This example shows that the branched isomers can be removed in a commercially feasible distillation process (head pressure 10 torr).

300 grams of mixed methyl cyanovalerates were used as feed to a batch, 20 plates 1 inch Oldershaw still with a 500 ml pot. The composition of the feed material as analyzed by GC was found to be 14.3% M4CV, 7.7% M3CV and 75.9% M5CV, with the remainder primarily acetals from methanol and 5FVN. The distillation began at total reflux at 10 torr ($1.3 \times 10^{-3}$ MPa) with a 0° C. condenser. The low boilers left the column primarily through the condenser at total reflux. At total reflux, the column reached a steady condition with 150° C. pot and 102° C. at the head. Distillate was then removed in 5 ml cuts at 100:1 reflux ratio using a vapor splitting head. Over the course of 13 cuts, the head temperature rose from 102 to 122° C. The composition of the first 3 cuts showed no M5CV and between 50 and 70% M4CV, 5 to 8% M3CV with the remainder being lower boiling impurities. This showed that the branched isomers have a considerably higher vapor pressure than the linear cyanovalerate. The distillation was continued, and large fractions (25 grams each) of M5CV were taken overhead later in the run with greater than 99.5% linearity. The final pot sample (which was 26 grams of the starting 300 grams) showed 0.14% M4CV and no detectable M3CV. The high boiler production in this 48 hour distillation was only 1% of the initial M5CV. The head temperature of the still leveled at 123° C. at 10 torr, which agrees with literature references for the vapor pressure of M5CV. This represents a greater than 20 degree difference in boiling point between the M4CV and the M5CV.

Example 3

Synthesis of Methyl 6-aminocaproate Using Raney Cobalt Catalyst

This example shows that methyl 5-cyanovalerate can be hydrogenated to methyl 6-aminocaproate in the presence of Raney® Cobalt.

A 100 mL stainless steel high pressure stirred reactor (Parr reactor) was charged with 26.0 g of methanol and 0.5 g of Raney® Cobalt 2724 (W. R. Grace). The reactor was then assembled by securing the cup to the head, pressure tested with 100 psig of nitrogen, and purged with hydrogen. It was then pressurized to 250 psig with hydrogen and heated up to the reaction temperature (75° C.) under constant stirring. 10.23 g of methyl-5-cyanovalerate (M5CV), 0.5 g of 1-methyl-2-pyrrolidinone (internal standard), and 5.0 g of methanol were added from a pre-charged addition cylinder to the reactor by pressurizing the addition cylinder with hydrogen. The pressure in the reactor was then brought up to the desired level (500 psig, 3.5 MPa) and maintained at that level throughout the entire duration of the run (1.2 hr). During the course of the reaction, 1 mL samples were withdrawn periodically from the reactor through a sample port connected to a dip leg inside the reactor. The samples were analyzed by gas chromatography with a Restex -5 Amine column (15 m×0.25 mm). The conversion of M5CV, selectivities and yields of 6-methyl aminocaproate (6MAC) and caprolactam (CL) as a function of time are shown in Table 2.

TABLE 2

| Time (hr) | M5CV Conversion (%) | 6MAC Selectivity (mole %) | 6MAC Yield (mole %) | CL Selectivity (mole %) | CL Yield (mole %) |
|---|---|---|---|---|---|
| 0.0 | 6.1 | 66.6 | 4.1 | 0.0 | 0.0 |
| 0.2 | 39.1 | 89.5 | 35.0 | 9.9 | 3.9 |
| 0.6 | 89.0 | 84.2 | 74.9 | 1.7 | 1.6 |
| 1.2 | 89.4 | 83.0 | 82.5 | 9.3 | 9.2 |

Example 4

Synthesis of Methyl 6-aminocaproate using Raney® Nickel Catalyst

The purpose of this example is to show that methyl 5-cyanovalerate can be hydrogenated to methyl 6-aminocaproate in the presence of Raney Nickel.

A 100 mL stainless steel high pressure stirred reactor (Parr reactor) was charged 26.0 g of methanol and 0.25 g of Raney® Ni 2400 (W. R. Grace). The reactor was then assembled by securing the cup to the head, pressure tested with 100 psig (0.7 MPa) of nitrogen, and purged with hydrogen. It was then pressurized to 250 psig (1.75 MPa) with hydrogen and heated up to the reaction temperature (70° C.) under constant stirring. 10.0 g of methyl 5-cyanovalerate (M5CV), 0.5 g of 1-methyl-2-pyrrolidinone (NMP, internal standard), and 5.0 g of methanol were added from a pre-charged addition cylinder to the reactor by pressurizing the addition cylinder with hydrogen. The pressure in the reactor was then brought up to the desired level (500 psig, 3.5 MPa) and maintained at that level throughout the entire duration of the run (3.9 hr). During the course of the reaction, samples (1.0 mL) were withdrawn periodically from the reactor through a sample port, connected to a dip leg inside the reactor. The samples were analyzed by gas chromatography with a Restex -5 Amine column (15 m×0.25mm). The conversion of M5CV, selectivities and yields of 6-methyl aminocaproate (GMAC) and caprolactam (CL) as a function of time are shown in Table 3.

TABLE 3

| Time (hr) | M5CV Conversion (%) | 6MAC Selectivity (mole %) | 6MAC Yield (mole %) | CL Selectivity (mole %) | CL Yield (mole %) |
|---|---|---|---|---|---|
| 0.0 | 1.6 | 59.3 | 1.0 | 0.0 | 0.0 |
| 0.3 | 7.3 | 96.6 | 7.0 | 0.8 | 0.1 |
| 1.1 | 16.4 | 94.1 | 15.4 | 1.0 | 0.2 |
| 2.1 | 26.4 | 87.7 | 23.1 | 2.0 | 0.5 |
| 3.4 | 31.8 | 85.0 | 27.0 | 3.3 | 1.0 |
| 3.9 | 43.2 | 78.4 | 33.9 | 6.6 | 2.8 |

What is claimed:

1. A process for making alkyl 6-aminocaproate comprising:
   (a) reacting 3-pentenenitrile with carbon monoxide and hydrogen in the presence of a hydroformylation catalyst comprising a Group VIII metal to produce a first reaction product which comprises 3-, 4-, and 5-formylvaleronitrile (FVN);
   (b) isolating from the first reaction product a FVN mixture consisting essentially of 3-, 4-, and 5-formylvaleronitrile;
   (c) reacting the FVN mixture to produce a second reaction product which comprises alkyl 3-, 4-, and 5-cyanovalerate by either:
      (i) contacting the FVN mixture with an alcohol, a molecular oxygen-containing gas, and a palladium-containing catalyst for a time sufficient to oxidize the FVN mixture to produce the second reaction product, or
      (ii) oxidizing the FVN mixture in the presence of a molecular oxygen-containing gas for a time sufficient to oxidize the FVN mixture to produce an oxidation product comprising 3-, 4-, and 5-cyanovaleric acid, and reacting the oxidation product with an alcohol to produce the second reaction product;
   (d) isolating the alkyl 5-cyanovalerate by distillation; and
   (e) reacting alkyl 5-cyanovalerate with hydrogen in the presence of a hydrogenation catalyst to produce a third reaction product which comprises alkyl 6-aminocaproate, in which the alkyl group contains the same number of carbon atoms as the alcohol.

2. The process of claim 1 in which the alcohol is a linear or branched $C_1$ to $C_{12}$ alkyl alcohol.

3. The process of claim 2 in which the alcohol is methanol or ethanol.

4. The process of claim 3 in which the hydroformylation catalyst is a rhodium compound.

5. The process of claim 4 in which the hydroformylation catalyst further comprises a ligand selected from the group consisting of phosphine, phosphonites, phosphinites, phosphites, and polydentate phosphites.

6. The process of claim 5 in which step (a) is performed at 50 to 150° C., a pressure of 0.15 to 10 MPa, a mole ratio of hydrogen to carbon monoxide of 100:1 to 1:10, and a mole ratio of 3-pentenenitrile to catalyst of 500:1 to 10,000:1.

7. The process of claim 6 wherein a single stage flash evaporator is used to isolate the FVN mixture from the first reaction product.

8. The process of claim 7 in which the molecular oxygen-containing gas is air.

9. The process of claim 8 in which step (c) is conducted at a temperature from 20 to 120° C. and at a pressure in excess of 10 bars (1 MPa).

10. The process of claim 9 in which the step (c) is carried out at a temperature from 40 to 80° C. and at a pressure of 20 to 40 bars (2 to 4 MPa).

11. The process of claim 10 in which alkyl 5-cyanovalerate is isolated from the second reaction product by fractional distillation.

12. The process of claim 11 in which step (d) is carried out at a pressure between $1.3 \times 10^{-3}$ and $6.5 \times 10^{-2}$ MPa and at a temperature between 100 and 250° C.

13. The process of claim 12 in which step (d) is carried out at a pressure between $6.5 \times 10^{-3}$ and $3.5 \times 10^{-2}$ MPa and the temperature is between 140 and 200° C.

14. The process of claim 13 in which the hydrogenation catalyst comprises at least one element selected from the group consisting of iron, ruthenium, rhodium, iridium, palladium, cobalt, nickel, chromium, osmium, and platinum.

15. The process of claim 14 in which the hydrogenation catalyst is selected from the group consisting of sponge cobalt, sponge nickel, and ruthenium metal on a solid support.

16. The process of claim 15 wherein the sponge cobalt or sponge nickel catalyst contains at least one promoter selected from the group consisting of lithium, sodium, potassium, copper, silver, gold, titanium zirconium, vanadium, chromium, molybdenum, tungsten, manganese, rhenium, iron, cobalt, nickel, ruthenium, rhodium, palladium, osmium, iridium, and platinum, wherein the promoter is present in an amount equal to or less than 10% by weight of the sponge catalyst.

17. The process of claim 16 wherein the step (e) is performed at a hydrogen pressure of 1.7 to 5.2 MPa, a molar ratio of hydrogen to alkyl 5-cyanovalerate of 2:1 to 100:1, and in the presence of a solvent comprising ammonia, methanol, water, or mixtures thereof.

18. The process of claim 15 in which the hydrogenation catalyst is ruthenium metal on a solid support selected from the group consisting of titanium dioxide, aluminum oxide, zirconium dioxide, and activated charcoal.

19. The process of claim 18 wherein the solid support is titanium dioxide.

20. The process of claim 1 further comprising:
   (f) cyclizing alkyl 6-aminocaproate to form a fourth reaction product comprising caprolactam, and
   (g) isolating caprolactam from the fourth reaction product.

* * * * *